United States Patent
Huang et al.

(10) Patent No.: US 7,452,528 B2
(45) Date of Patent: *Nov. 18, 2008

(54) PEPTIDE-BASED CARBON NANOTUBE HAIR COLORANTS AND THEIR USE IN HAIR COLORANT AND COSMETIC COMPOSITIONS

(75) Inventors: Xueying Huang, Hockessin, DE (US); Robert K. Kobos, Wilmington, DE (US); Gann Xu, Boothwyn, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/093,873

(22) Filed: Mar. 30, 2005

(65) Prior Publication Data
US 2005/0229335 A1    Oct. 20, 2005

Related U.S. Application Data

(60) Provisional application No. 60/562,645, filed on Apr. 15, 2004.

(51) Int. Cl.
A61K 8/64    (2006.01)
A61Q 5/00    (2006.01)
C07K 2/00    (2006.01)

(52) U.S. Cl. .............. 424/70.6; 424/70.1; 424/70.14; 530/345

(58) Field of Classification Search ............ None
See application file for complete search history.

(56) References Cited

U.S. PATENT DOCUMENTS

| | | | |
|---|---|---|---|
| 4,559,057 A | 12/1985 | Bogaty et al. | |
| 5,597,386 A | 1/1997 | Igarashi et al. | |
| 7,220,405 B2* | 5/2007 | Huang et al. | 424/70.6 |
| 2002/0034480 A1 | 3/2002 | Grimm et al. | |
| 2002/0041854 A1 | 4/2002 | Hadasch et al. | |
| 2003/0039604 A1 | 2/2003 | Niu et al. | |
| 2003/0185870 A1 | 10/2003 | Grinstaff et al. | |
| 2004/0010864 A1 | 1/2004 | Vic et al. | |
| 2004/0115232 A1* | 6/2004 | Giroud et al. | 424/401 |
| 2005/0050656 A1 | 3/2005 | Huang et al. | |

OTHER PUBLICATIONS

Pantarotto et al. Synthesis, Structural Characterization, and Immunological Properties of Carbon Nanotubes Functionalized with Peptides. Journal of the American Chemical Society. Apr. 23, 2003, vol. 125, No. 20, pp. 6160-6164.*

Francisco Carrasco-Marin et al., Water adsorption on activated carbons with different degrees of oxidation, J. Chem. Soc., Faraday Trans., vol. 93(12):2211-2215, 1997.

Eric Langenmayr et al., Carbon Black Dispersions For High Optical Density on Plain Paper, IS&T's NIP19:2003 International Conference on Digital Printing Technologies, pp. 199-202.

Yongfu Lian et al., Assignment of the Fine Structure in the Optical Absorption Spectra of Soluble Single-Walled Carbon Nanotubes, J. Phys. Chem. B, vol. 107:12082-12087, 2003.

* cited by examiner

*Primary Examiner*—Jeffrey E Russel

(57) ABSTRACT

Peptide-based carbon nanotube hair colorants are described. The hair colorants are prepared by coupling hair-binding peptides to the surface of chemically functionalized carbon nanotubes. Hair colorant and cosmetic compositions comprising the peptide-based carbon nanotube colorants are also described.

23 Claims, 1 Drawing Sheet

Figure 1:
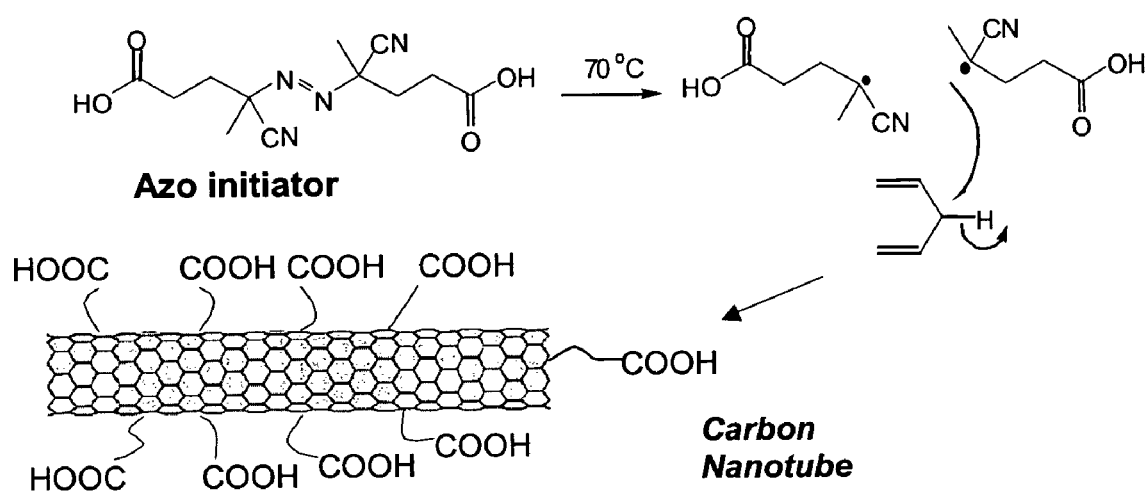

SEQUENCE LISTING

<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 1

Arg Thr Asn Ala Ala Asp His Pro Ala Ala Val Thr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 2

Asn Thr Ser Gln Leu Ser Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 3

Thr Pro Pro Glu Leu Leu His Gly Asp Pro Arg Ser
1               5                   10

<210> SEQ ID NO 4
<211> LENGTH: 12
<212> TYPE: PRT

```
<213> ORGANISM: Artificial Sequence
<220> FEATURE:
<223> OTHER INFORMATION: Hair-binding peptide

<400> SEQUENCE: 4

Thr Pro Pro Thr Asn Val Leu Met Leu Ala Thr Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 5

Thr Ala Val Met Asn Val Val Asn Asn Gln Leu Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 6

Asp Leu Thr Leu Pro Phe His
1               5

<210> SEQ ID NO 7
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 7

Ala Pro Pro Ala Thr Pro Ala Ala Leu Val Gln Pro
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 8

Leu Glu Ser Gly Asp Glu Val Asp
1               5
```

PEPTIDE-BASED CARBON NANOTUBE HAIR COLORANTS AND THEIR USE IN HAIR COLORANT AND COSMETIC COMPOSITIONS

This application claims the benefit of U.S. Provisional Application 60/562,645, filed on Apr. 15, 2004.

FIELD OF THE INVENTION

The invention relates to the field of personal care products. More specifically, the invention relates to peptide-based carbon nanotube hair colorants, formed by coupling a hair-binding peptide to carbon nanotubes, and their use in hair colorant and cosmetic compositions.

BACKGROUND OF THE INVENTION

Hair coloring compositions contain various types of coloring agents, specifically, permanent, semi-permanent or direct, and temporary colorants. The permanent hair dyes are generally oxidative dyes that provide hair color that lasts about four to six weeks. These oxidative hair dyes consist of two parts; one part contains the oxidative dyes in addition to other ingredients, while the second part contains an oxidizing agent such as hydrogen peroxide. The two components are mixed immediately prior to use. The oxidizing agent oxidizes the dye precursors, which then combine to form large color molecules within the hair shaft. Although the oxidative hair dyes provide long-lasting color, the oxidizing agents they contain cause hair damage. The semi-permanent or direct hair dyes are preformed dye molecules that are applied to the hair and provide color for about six to twelve shampoos. This type of hair dye is gentler to the hair because it does not contain peroxides, but the hair color does not last as long. Temporary hair dyes are dye molecules or pigments that are too large to diffuse into the hair shaft, and therefore act on the exterior of the hair. Consequently, temporary hair dyes are generally removed after one or two shampoos.

Carbon black has been used as a temporary hair dye in hair coloring compositions, particularly for covering white or gray hair (Bogaty et al., U.S. Pat. No. 4,559,057). Additionally, carbon black has been used as a pigment in cosmetic formulations such as eye shadow, eyeliner, and mascara (Hadasch et al., U.S. Patent Application Publication No. 2002/0041854, and Grimm et al., U.S. Patent Application Publication No. 2002/0034480). Carbon black provides good covering properties, but has a weak interaction with the hair so that the adherence of the pigment to the hair is poor. Consequently, the carbon black color is readily transferred to clothing, skin, combs, brushes, and other contacting surfaces. To enhance the interaction of the carbon black pigment with hair, Igarashi et al. (U.S. Pat. No. 5,597,386) used anti-hair antibody attached to carbon black as a hair colorant. Although this method results in stronger attachment of the carbon black to hair, the antibodies are expensive and difficult to produce. Huang et al (copending, commonly owned U.S. patent application Ser. No. 10/935,642) describe hair colorants comprising hair-binding peptides coupled to carbon black and other pigments. The hair-binding peptides bind strongly to the hair to give a more durable hair coloring effect.

Carbon nanotubes (CNT) have been the subject of intense research since their discovery in 1991. Carbon nanotubes possess unique properties such as small size, considerable stiffness, and electrical conductivity, which make them suitable in a wide range of applications. Carbon nanotubes may be either multi-walled (MWNT) or single-walled (SWNT), and have diameters in the nanometer range. The use of chemically functionalized or physically modified carbon nanotubes as a hair colorant is described by Huang et al. (copending, commonly owned U.S. Patent Application No. (60/562,507). The nanotubes provide an enhanced interaction with the hair to give a more durable coloring effect. However, more durable hair colorants are still needed.

Therefore, the need exists for a black pigment for use in hair coloring and cosmetic compositions that has enhanced interaction with hair fibers to give a more durable coloring effect.

Applicants have solved the stated problem by discovering that hair-binding peptide-carbon nanotube hair colorants function as an effective black pigment in hair coloring and cosmetic compositions. The peptide-based carbon nanotube colorants provide significant advantages for high performance hair coloring without damaging the hair. The small size of the nanotubes, typically, a few nanometers in diameter, provides a thin coating that results in a smooth feeling to the hair, while producing a volumizing effect. Additionally, the strong affinity of the hair-binding peptide for hair results in a longer-lasting coloring effect.

SUMMARY OF THE INVENTION

The invention provides peptide-based carbon nanotube hair colorants. In one embodiment, the peptide-based carbon nanotube hair colorants are diblock compositions having the general structure $(HBP)_n$-CNT, wherein
  a) HBP is a hair-binding peptide;
  b) CNT is a carbon nanotube; and
  c) n ranges from 1 to about 500.

In another embodiment, the peptide-based carbon nanotube hair colorants are triblock compositions having the general structure $[(HBP)_m\text{-}S]_n$-CNT, wherein
  a) HBP is a hair-binding peptide;
  b) CNT is a carbon nanotube;
  c) S is a spacer;
  d) m ranges from 1 to about 50; and
  e) n ranges from 1 to about 500.

In an alternate embodiment the invention provides peptide-based carbon nanotube hair colorants wherein the chemically functionalized carbon nanotube is produced by a process comprising the steps of:
  a) providing a population of undispersed carbon nanotubes in solution;
  b) contacting the carbon nanotubes of (a) with a radical generating agent in the presence of acid for a time sufficient to permit the carbon nanotubes to disperse; and
  c) optionally recovering the carbon nanotubes.

In another alternate embodiment the invention provides peptide-based carbon nanotube hair colorants wherein the hair binding peptide is selected by a process comprising the steps of:
  a) providing a library of combinatorial generated peptides;
  b) contacting the library of (a) with a hair sample to form a reaction solution comprising peptide-hair complexes:
  c) isolating the peptide-hair complex of (b) from the reaction solution;
  d) amplifying the DNA encoding the peptide portion of the peptide-hair complex of (c); and
  e) sequencing the amplified DNA of (d) encoding a hair-binding peptide wherein the hair-binding peptide is selected.

In another embodiment the invention provides a method for coloring hair, eyebrows or eyelashes comprising the steps of:

a) providing a colorant composition selected from the group consisting of:
  i) $(HBP)_n$-CNT; and
  ii) $[(HBP)_m$-$S]_k$-CNT
  wherein
   1) HBP is a hair-binding peptide;
   2) CNT is a carbon nanotube;
   3) n ranges from 1 to about 500
   4) S is a spacer;
   5) m ranges from 1 to about 50; and
   6) k ranges from 1 to about 500;
  and wherein the hair binding peptide is selected by a method comprising the steps of:
   A) providing a library of combinatorial generated peptides;
   B) contacting the library of (A) with a hair sample to form a reaction solution comprising peptide-hair complexes:
   C) isolating the peptide-hair complex of (B) from the reaction solution;
   D) amplifying the DNA encoding the peptide portion of the peptide-hair complex of (C); and
   E) sequencing the amplified DNA of (D) encoding a hair-binding peptide wherein the hair-binding peptide is selected; and
b) contacting the colorant composition of (a) with hair, eyebrows or eyelashes for a time sufficient for the peptide-based carbon nanotube colorant to bind to hair, eyebrows or eyelashes.

Additionally, the invention provides hair colorant and cosmetic compositions comprising peptide-based carbon nanotube colorants. Methods of using these compositions to dye hair and color eyebrows and eyelashes are also provided.

BRIEF DESCRIPTION OF THE FIGURES AND SEQUENCE DESCRIPTIONS

The invention can be more fully understood from the following detailed description, figure and the accompanying sequence descriptions, which form a part of this application.

FIG. 1 illustrates the mechanism of the chemical functionalization of the surface of a carbon nanotube using an azo-initiator.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-7 are the amino acid sequences of hair-binding peptides.

SEQ ID NO. 8 is the amino acid sequence of the Caspase 3 cleavage site.

DETAILED DESCRIPTION OF THE INVENTION

The invention provides peptide-based carbon nanotube hair colorants and hair colorant and cosmetic compositions comprising these colorants. The peptide-based carbon nanotube colorants provide significant advantages for high performance hair coloring without damaging the hair. The small size of the nanotubes, typically, a few nanometers in diameter, provides a thin coating that results in a smooth feeling to the hair, while producing a volumizing effect. Additionally, the strong affinity of the hair-binding peptide for hair results in a longer-lasting coloring effect. The invention is useful because the hair colorant and cosmetic compositions comprising hair-binding peptide-carbon nanotube hair colorants have use in various personal care products, including, but not limited to, hair colorants, eye shadow, eyeliner, eyebrow pencil, and mascara.

The following definitions are used herein and should be referred to for interpretation of the claims and the specification.

"CNT" means carbon nanotube.
"MWNT" means multi-walled nanotube.
"SWNT" means single walled nanotube.
"HBP" means hair-binding peptide.
"S" means spacer.

The term "peptide" refers to two or more amino acids joined to each other by peptide bonds or modified peptide bonds.

The term "hair" as used herein refers to human hair, eyebrows, and eyelashes.

The terms "coupling" and "coupled" as used herein refer to any chemical association and includes both covalent and non-covalent interactions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments, which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters, which cause a gene to be expressed in most cell types, at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The instant invention provides peptide-based carbon nanotube hair colorants and hair colorant and cosmetic compositions comprising these colorants. The peptide-based carbon nanotube hair colorants are formed by coupling a hair-binding peptide to carbon nanotubes. In another embodiment, the hair-binding peptide is coupled to carbon nanotubes via a spacer.

Hair-Binding Peptides

The hair-binding peptides of the present invention are from about 7 amino acids to about 45 amino acids, in addition, from about 7 amino acids to about 20 amino acids, and further in addition, from about 7 to about 12 amino acids. Suitable hair-binding peptides may be selected using a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500). Techniques to generate such biological peptide libraries are described in Dani, M., *J. of Receptor & Signal Transduction Res.*, 21 (4):447-468 (2001).

A preferred method to randomly generate hair-binding peptides is by phage display, as described by Huang et al. in copending, commonly owned U.S. patent application Ser. No. 10/935,642, which is incorporated herein by reference. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

After a suitable library of peptides has been generated, they are then contacted with an appropriate amount of the test substrate, specifically a hair sample. The library of peptides is dissolved in a suitable solution for contacting the hair sample. The hair sample may be suspended in the solution or may be immobilized on a plate or bead. A preferred solution is a buffered aqueous saline solution containing a surfactant, for example, Tris-buffered saline (TBS) with 0.5% Tween® 20. The solution may be agitated by any means in order to increase the mass transfer rate of the peptides to the hair surface, thereby shortening the time required to attain maximum binding.

Upon contact, a number of the randomly generated peptides bind to the hair to form a phage-peptide-hair complex. Unbound phage-peptide may be removed by washing. After all unbound material is removed, phage-peptides having varying degrees of binding affinities for hair may be fractionated by selected washings in buffers having varying stringencies. Increasing the stringency of the buffer used increases the required strength of the bond between the peptide and substrate in the phage-peptide-hair complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, Tween® 20, wherein Tween® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage-peptides having increasing binding affinities for hair may be eluted by repeating the selection process using buffers with increasing stringencies. Additionally, some elution resistant phage-peptides may remain bound to the hair after the elution steps. The eluted phage-peptides and/or the remaining bound elution resistant phage peptides may be amplified, as described below, and sequenced by any means known in the art.

Thus, in one embodiment the following general method for generating the hair-binding peptides of the present invention may be used. A library of combinatorial generated peptides is contacted with a hair sample to form peptide-hair complexes. The peptide-hair complex is separated from uncomplexed peptides and unbound hair, and the bound peptides from the peptide-hair complexes are eluted from the complex, preferably by acid treatment. Then, the eluted peptides are identified and sequenced. To identify peptide sequences that bind to one substrate but not to another, e.g., peptides that bind to hair, but not to skin, a subtractive panning step is added.

Specifically, the library of combinatorial generated peptides is first contacted with the non-target to remove phage-peptides that bind to it. Then, the non-binding peptides are contacted with hair and the above process is followed. Alternatively, the library of combinatorial generated peptides may be contacted with the non-target and the desired substrate simultaneously. Then, the peptide-hair complexes are separated from the peptide-non-target complexes and the method described above is followed for the desired peptide-hair complexes.

In another embodiment, hair-binding peptides with a high hair-binding affinity may be selected using the following method. A library of combinatorial generated peptides is contacted with a hair sample to form a reaction solution comprising peptide-hair complex, unbound hair, and uncomplexed peptides. The peptide-hair complex is isolated from the reaction solution. The weakly bound peptides are eluted from the peptide-hair complex, preferably by acid treatment. Then, the remaining, elution-resistant peptide-hair complexes are used to directly infect a bacterial host cell, such as *E. coli* ER2738, as described by Huang et. al. (U.S. patent application Ser. No. 10/935,642). The infected host cells are grown in a suitable growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for hair. Alternatively, the remaining bound peptides may be amplified using a nucleic acid amplification technique, such as the polymerase chain reaction (PCR). In that approach, PCR is carried out on the remaining bound peptides using the appropriate primers, as described by Janssen et al. in U.S. Patent Application Publication No. 2003/0152976, which is incorporated herein by reference. Additionally, both the eluted peptides and the remaining bound peptides may be amplified simultaneously using the methods described above. The amplified peptides are then sequenced to identify the peptide sequences with a binding affinity for hair.

Examples of suitable hair-binding peptides include, but are not limited to SEQ ID NOs:1-7.

Production of Hair-Binding Peptides

The hair-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services. Alternatively, the peptides of the invention may be prepared using recombinant DNA and molecular cloning techniques. Genes encoding the hair-binding peptides may be produced in heterologous host cells, particularly in the cells of microbial hosts.

Preferred heterologous host cells for expression of the hair-binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the hair-binding peptides of the invention. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the hair-binding peptides of the present invention. These chimeric genes could then be introduced into appropriate microorganisms via transformation to provide high level expression of the hair-binding peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*. Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOXI (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the hair-binding peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Carbon Nanotubes

The term "carbon nanotube" refers to a hollow article composed primarily of carbon atoms. Carbon nanotubes of the invention are generally about 0.5 to 2 nm in diameter where the ratio of the length dimension to the narrow dimension (diameter), i.e., the aspect ratio, is at least 5. In general, the aspect ratio is between 10 and 2000. Carbon nanotubes are comprised primarily of carbon atoms, however they may be doped with other elements, e.g., metals. The carbon-based nanotubes of the invention can be either multi-walled nanotubes (MWNTs) or single-walled nanotubes (SWNTs). A MWNT, for example, includes several concentric nanotubes each having a different diameter. Thus, the smallest diameter tube is encapsulated by a larger diameter tube, which in turn, is encapsulated by another larger diameter nanotube. A SWNT, on the other hand, includes only one nanotube.

Carbon nanotubes may be produced by a variety of methods, and are commercially available, for example from Carbon Nanotechnologies Inc. (Houston, Tex.) and Carbon Solutions Inc. (Riverside, Calif.). Methods of CNT synthesis include laser vaporization of graphite (A. Thess et al., *Science* 273, 483 (1996)), arc discharge (C. Journet et al., *Nature* 388, 756 (1997)) and HiPCo (high pressure carbon monoxide) process (P. Nikolaev et al. *Chem. Phys. Lett.* 313, 91-97 (1999)). Chemical vapor deposition (CVD) can also be used in producing carbon nanotubes (J. Kong et al. *Chem. Phys. Lett.* 292, 567-574 (1998); J. Kong et al. *Nature* 395, 878-879 (1998); A. Cassell et al. *J. Phys. Chem.* 103, 6484-6492 (1999); H. Dai et al. *J. Phys. Chem.* 103, 11246-11255 (1999)).

Additionally CNTs may be grown via catalytic processes both in solution and on solid substrates (Yan Li, et al., *Chem. Mater.* 13(3), 1008-1014 (2001); N. Franklin and H. Dai *Adv. Mater.* 12, 890 (2000); and A. Cassell et al. *J. Am. Chem. Soc.* 121, 7975-7976 (1999)). Most CNTs, as presently prepared, are in the form of entangled tubes. Individual tubes in the product differ in diameter, chirality, and number of walls. Moreover, long tubes show a strong tendency to aggregate into "ropes" held together by Van der Waals forces. These ropes are formed due to the large surface areas of nanotubes and can contain tens to hundreds of nanotubes in one rope.

Chemically Functionalized Carbon Nanotubes

In order to facilitate coupling of the hair-binding peptides, the carbon nanotubes may be chemically functionalized using methods known in the art. The chemical functionalization of the carbon nanotube surface results in functional groups, including but not limited to —COOH, —PO$_4^-$, —SO$_3^-$, —SO$_3$H, —SH, NH$_2$, tertiary amines, quaternized amines, —CHO, or —OH.

In one embodiment, the undispersed carbon nanotubes are functionalized by oxidation according to the methods described by Niu et al. in U.S. Patent Application Publication Nos. 2003/0039604 and 2003/0086858, both of which are incorporated herein by reference. For example, the undispersed carbon nanotubes may be oxidized by contacting them with a radical generating agent, including but not limited to, ammonium persulfate ((NH$_4$)$_2$S$_2$O$_8$), sodium persulfate (Na$_2$S$_2$O$_8$), or potassium persulfate (K$_2$S$_2$O$_8$) in an acid. Suitable acids include, but are not limited to sulfuric acid, nitric acid, hydrochloric acid, or trifluoroacetic acid. This oxidation results in the generation of surface —COOH, —CHO, and —OH groups on the surface of the carbon nanotubes.

In another embodiment, the carbon nanotubes are functionalized utilizing a free radical organic initiator, for example azo-initiators. The reaction mechanism is shown in FIG. 1. Carbon nanotubes are hollow tubes with conjugated surface structure (C═C bonds). The 2,2'-Azobis(4-cyanovaleric acid) is decomposed at a certain temperature (70° C.) to form free radicals. The free radicals attack the double bond (C═C) on carbon nanotubes to form a single C—C bond and the carbon nanotube surface is covalently linked with the acid functional groups. Such acid functionalized carbon nanotubes are dispersed in organic and aqueous solutions. The free radical functionalization of the carbon nanotube surface results in functional groups, including but not limited to, —COOH, —PO$_4^-$, —SO$_3^-$, —SO$_3$H, —SH, NH$_2$, tertiary amines, quaternized amines, —CHO, or —OH.

In another embodiment, a Diels-Alder reaction is used to functionalize the surface of carbon nanotubes. A Diels-Alder reaction is a chemical reaction between a conjugated molecule and a C═C bond molecule under certain conditions, as shown below. Since carbon nanotubes have conjugated surface structure, this reaction can be adopted to chemically attach functional groups to the surface of carbon nanotube to make the tubes well dispersed in organic or aqueous solutions. Chemical functionalization by Diels-Alder reaction results in functional groups on carbon nanotubes, including but not limited to, —COOH, —PO$_4^-$, —SO$_3^-$, —SO$_3$H, —SH, NH$_2$, tertiary amines, quaternized amines, —CHO, or —OH.

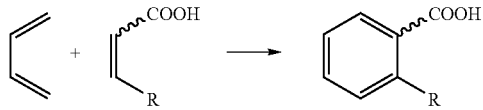

Peptide-Based Carbon Nanotube Hair Colorants

The peptide-based carbon nanotube hair colorants of the present invention are prepared by coupling a specific hair-binding peptide (HBP) to carbon nanotubes (CNT), either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based hair colorant may be prepared by mixing the peptide with the carbon nanotubes and the optional spacer (if used) and allowing sufficient time for the interaction to occur. The unbound materials may be separated from the resulting peptide-based hair colorant adduct using methods known in the art, for example, gel permeation chromatography.

The peptide-based hair colorants of the invention may also be prepared by covalently attaching a specific hair-binding peptide to carbon nanotubes, either directly or through a spacer. Any known peptide or protein conjugation chemistry may be used to couple the hair-binding peptide to the functionalized carbon nanotubes. Conjugation chemistries are well known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid terminal groups on the peptides and to amine, carboxylic acid, or alcohol groups on the carbon nanotubes. The preferred coupling agents are carbodiimide coupling agents, such as 1-ethyl-3-(3-dimethylaminopropyl)-carbodiimide (EDC) and N,N'-dicyclohexylcarbodiimide (DCC), which may be used to activate carboxylic acid groups for coupling to alcohol, and amine groups. Additionally, it may be necessary to protect reactive amine or carboxylic acid groups on the peptide to produce the desired structure for the peptide-based carbon nanotube hair colorant. The use of protecting groups for amino acids, such as t-butyloxycarbonyl (t-Boc), are well known in the art (see for example Stewart et al., supra; Bodanszky, supra; and Pennington et al., supra).

It may also be desirable to couple the hair-binding peptide to the carbon nanotubes via a spacer. The spacer serves to separate the carbon nanotube from the peptide to ensure that the carbon nanotube does not interfere with the binding of the peptide to the hair. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The spacer may be covalently attached to the hair-binding peptide and the carbon nanotube using any of the coupling chemistries described above. In order to facilitate incorporation of the spacer, a bifunctional cross-linking agent that contains a spacer and reactive groups at both ends for coupling to the peptide and the carbon nanotube may be used. Suitable bifunctional cross-linking agents are well known in the art and include, but are not limited to diamines, such as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

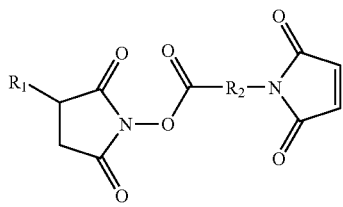

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine or alcohol groups on the carbon nanotube, while the maleimide group reacts with thiol groups present on the peptide. A thiol group may be incorporated into the peptide by adding a cysteine group to at least one end of the binding peptide sequence (i.e., the C-terminus or N-terminus). Several spacer amino acid residues, such as glycine, may be incorporated between the binding peptide sequence and the terminal cysteine to separate the reacting thiol group from the binding sequence.

Additionally, the spacer may be a peptide comprising any amino acid or mixtures thereof. The preferred peptide spacers are composed of the amino acids glycine, alanine, and serine, and mixtures thereof. In addition, the peptide spacer may contain a specific enzyme cleavage site, such as the protease Caspase 3 site, given by SEQ ID NO:8, which allows for the enzymatic removal of the carbon nanotubes from the hair. The peptide spacer may be from 1 to about 50 amino acids, preferably from 1 to about 20 amino acids. These peptide spacers may be linked to the binding peptide sequence by any method know in the art. For example, the entire binding peptide-peptide spacer diblock may be prepared using the standard peptide synthesis methods described supra. In addition, the binding peptide and peptide spacer blocks may be combined using carbodiimide coupling agents (see for example, *Hermanson, Bioconjugate Techniques*, Academic Press, New York (1996)), diacid chlorides, diisocyanates and other difunctional coupling reagents that are reactive to terminal amine and/or carboxylic acid terminal groups on the peptides. Alternatively, the entire binding peptide-peptide spacer diblock may be prepared using the recombinant DNA and molecular cloning techniques described supra. The spacer may also be a combination of a peptide spacer and an organic spacer molecule, which may be prepared using the methods described above.

It may also be desirable to have multiple hair-binding peptides coupled to the carbon nanotube to enhance the interaction between the peptide-based hair colorant and the hair. Either multiple copies of the same hair-binding peptide or a combination of different hair-binding peptides may be used. Due to the large surface area of the carbon nanotubes, a large number of hair-binding peptides may be coupled to a single nanotube i.e., up to about 500. Therefore, in one embodiment of the present invention, the peptide-based hair colorants are diblock compositions comprising a hair-binding peptide (HBP) and a carbon nanotube (CNT), having the general structure $(HBP)_n$-CNT, where n ranges from 1 to about 500, preferably n is 1 to about 50. In another embodiment, the peptide-based carbon nanotube hair colorants contain a spacer (S) separating the binding peptide from the carbon nanotube, as described above. Multiple copies of the hair-binding peptide may be coupled to a single spacer molecule. In this embodiment, the peptide-based carbon nanotube colorants are triblock compositions comprising a hair-binding peptide, a spacer, and a carbon nanotube, having the general structure $[(HBP)_m\text{-}S]_n$-CNT, where n ranges from 1 to about 500, preferably n is 1 to about 50, and m ranges from 1 to about 50, preferably m is 1 to about 10.

It should be understood that as used herein, HBP is a generic designation and is not meant to refer to a single hair binding peptide sequence. Where n or m as used above, is greater than 1, it is well within the scope of the invention to provide for the situation where a series of hair binding peptides of different sequences may form a part of the composition. Additionally, it should be understood that these structures do not necessarily represent a covalent bond between the peptide, the carbon nanotube, and the optional spacer. As described above, the coupling interaction between the peptide, the carbon nanotube, and the optional spacer may be either covalent or non-covalent.

Hair Colorant Compositions

The hair colorant compositions of the invention comprise an effective amount of a peptide-based carbon nanotube hair colorant in a cosmetically acceptable medium. An effective amount of a peptide-based carbon nanotube hair colorant for use in hair colorant compositions is herein defined as a proportion of from about 0.001% to about 20% by weight relative to the total weight of the composition. Components of a cosmetically acceptable medium for hair colorant compositions are well known in the art (see for example Dias et al., in U.S. Pat. No. 6,398,821, Deutz et al., in U.S. Pat. No. 6,129,770, and Bogaty et al. in U.S. Pat. No. 4,559,057, all of which are incorporated herein by reference). For example, hair colorant compositions may be aqueous solutions or aqueous alcoholic solutions and may contain sequestrants, stabilizers, thickeners, buffers, carriers, surfactants, solvents, antioxidants, polymers, and conditioners. In contrast to oxidative hair colorant compositions which require strong alkaline conditions, the hair colorant compositions of the invention may have a neutral or near-neutral pH, i.e., pH 6 to 8.

Methods for Dyeing Hair

The present invention also provides methods for coloring hair by applying a hair colorant composition comprising an effective amount of a peptide-based carbon nanotube hair colorant to the hair by various means, including, but not limited to, spraying, brushing, or applying by hand. The hair colorant composition is allowed to contact the hair for a period of time sufficient for the peptide-based carbon nanotube colorant to bind to the hair, typically between about 5 to about 50 min, and then the hair colorant composition may be rinsed from the hair. In one embodiment, the application of the hair colorant composition to the hair is repeated one or more times. In addition to coloring hair, the peptide-based carbon nanotube colorants of the invention provide a volumizing (i.e., thickening) effect on the hair.

In a preferred embodiment for hair dying the hair binding peptides are selected by the phage display method. Thus it is within the scope of the invention to provide a method for coloring hair, eyebrows or eyelashes comprising the steps of:
a) providing a colorant composition selected from the group consisting of:
  i) $(HBP)_n$-CNT; and
  ii) $[(HBP)_m\text{-}S]_k$-CNT
  wherein
    1) HBP is a hair-binding peptide;
    2) CNT is a carbon nanotube;

3) n ranges from 1 to about 500

4) S is a spacer;

5) m ranges from 1 to about 50; and 6) k ranges from 1 to about 500;

and wherein the hair binding peptide is selected by a method comprising the steps of:

A) providing a library of combinatorial generated peptides;

B) contacting the library of (A) with a hair sample to form a reaction solution comprising peptide-hair complexes:

C) isolating the peptide-hair complex of (B) from the reaction solution;

D) amplifying the DNA encoding the peptide portion of the peptide-hair complex of (C); and E) sequencing the amplified DNA of (D) encoding a hair-binding peptide wherein the hair-binding peptide is selected; and b) contacting the colorant composition of (a) with hair, eyebrows or eyelashes for a time sufficient for the peptide-based carbon nanotube colorant to bind to hair, eyebrows or eyelashes.

Cosmetic Compositions

The peptide-based carbon nanotube hair colorants of the invention may also be used as coloring agents in cosmetic compositions including, but not limited to, eye shadow, eyeliner, eyebrow pencil, and mascara. Cosmetic compositions containing pigments are well known in the art (see for example, Philippe in U.S. Pat. No. 6,280,747, Arraudeau et al. in U.S. Pat. No. 5,053,220, and Grimm et al. in U.S. Patent Application Publication No. 2002/0034480, all of which are incorporated herein by reference).

In one embodiment, the cosmetic composition is an anhydrous make-up product comprising a cosmetically acceptable medium which contains a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. In another embodiment, the cosmetic composition is in the form of a stable dispersion such as a water-in-oil or oil-in-water emulsion. In both types of compositions, the effective amount of the peptide-based carbon nanotube colorant is generally from about 0.001% to about 20% by weight relative to the total weight of the composition.

Methods for Coloring Eyebrows or Eyelashes

The present invention also provides a method for coloring eyebrows or eyelashes by contacting a cosmetic composition comprising an effective amount of a peptide-based carbon nanotube colorant to the eyebrows or eyelashes by various means, including, but not limited to, spraying, brushing, or applying by hand. The cosmetic composition is allowed to contact the eyebrows or eyelashes for a period of time sufficient for the peptide-based carbon nanotube colorant to bind to the eyebrows or eyelashes. Typically, the composition is left on after the application. In one embodiment, the application of the cosmetic composition to the eyebrows or eyelashes is repeated one or more times. In addition to coloring eyebrows or eyelashes, the peptide-based carbon nanotube colorants of the invention provide a volumizing (i.e., thickening) effect on the eyebrows or eyelashes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "mL" means milliliter(s), "L" means liter(s), "μL" means microliter(s), "μm" means micrometer(s), "mol" means mole(s), "mmol" means millimole(s), "g" means gram(s), "mg" means milligram(s), "ppm" means parts per million, "M" means molar concentration. "rpm" means revolutions per minute, "qs" means as much as suffices.

Example 1

Preparation of a Peptide-Based Carbon Nanotube Hair Colorant

The purpose of this prophetic Example is to describe the preparation of a peptide-based carbon nanotube hair colorant by coupling a hair-binding peptide (SEQ ID NO:1) to the surface of chemically functionalized carbon nanotubes. The surface of the carbon nanotubes is functionalized by reaction with 2,2'-azobis(2methylpropionamide)-dihydrochloride to introduce free amino groups. The functionalized carbon nanotubes are then coupled to the specific hair-binding peptide.

Functionalization of Carbon Nanotube Surface:

Multi-walled carbon nanotubes (2.0 g, HiPCo from Carbon Nanotechnologies Inc., Houston, Tex.) and 1.0 g of 2,2'-Azobis(2-methylpropionamide)dihydrochloride (Aldrich, Milwaukee, Wis.) are added to a 100 mL round-bottom flask and 30 mL of dioxane is added. The flask is purged with nitrogen for 5 min. Then, the flask is sealed with a rubber septum and the reaction mixture is stirred at 65° C. for 14 h. After this time, 50 mL of deionized water, prepared with a Nanopure water purification system (Barnstead/Thermolyne, Dubuque, Iowa), is added to the mixture. The diluted solution is centrifuged to collect the functionalized carbon nanotubes and to remove the organic solvent and unreacted reagents. The nanotubes are washed with deionized water and centrifuged. This washing and centrifuging process are repeated 2 more times. The functionalized carbon nanotubes are then dried by lyophilization.

Synthesis of t-Boc-Protected Hair-Binding Peptide:

The purpose of this reaction is to protect the amino end group of the hair-binding peptide. The hair-binding peptide (0.25 g), given as SEQ ID NO:1, which may be obtained from SynPep, Dublin, Calif., is mixed with 2.5 mL of deionized water in a 25 mL round-bottom flask. Then, 20 mg of NaOH and 0.25 mL of t-butyl alcohol are added. After stirring the mixture for 2 min, 0.12 g of di-tert-butyl dicarbonate (t-Boc anhydride) (Aldrich) is added dropwise. The flask is sealed with a rubber septum and the reaction mixture is stirred overnight at room temperature. Upon addition of water (10 mL), the reaction mixture forms a milky emulsion, which is then extracted three times with 5 mL portions of methylene chloride. The organic layer is washed twice with 5 mL portions of deionized water. The clear water layers are all combined and dried by lyophilization. The product is analyzed by liquid chromatography-mass spectrometry (LC-MS).

Coupling of Amino-Functionalized Carbon Nanotubes with t-Boc-Peptide:

Amino-functionalized carbon nanotubes (87 mg), t-Boc-peptide (80 mg) and dicyclohexyl carbodiimide (22 mg) are added to 3 mL of tetrahydrofuran (THF). A solution of dimethyl aminopyridine (17 μL) in several drops of THF is added dropwise to this mixture with stirring. The resulting dark suspension is heated to 40° C. for 6 h with stirring, followed by stirring overnight at room temperature. Trifluoroacetic acid (0.6 mL) is added to the product and the mixture is stirred for another 6 h. Then, 5 mL of deionized water is added to the reaction mixture. The mixture is centrifuged at 3,500 rpm for 2 min and the supernatant is decanted. The solid remaining in the centrifuge tube is washed with deionized water and centrifuged again. This washing is repeated until the pH of the supernatant reaches approximately 6.0. The dark residue, which is the peptide-based carbon nanotube colorant, is then dried using a lyophilizer for 2 days.

Example 2

Hair Dyeing Using a Peptide-Based Carbon Nanotube Hair Colorant

The purpose of this prophetic Example is to describe the dyeing of a sample of natural white hair using the peptide-based carbon nanotube hair colorant, described in Example 1.

A bundle of natural white hair (approximately 100 pieces) (from International Hair Importers and Products Inc., Bellerose, N.Y.) is cleaned by mixing with 10 mL of 50% isopropanol for 30 min and then washed at least 5 times with distilled water. After drying in air, the cleaned hair is immersed for 30 min in a solution containing 50 mg of the peptide-based carbon nanotube hair colorant, which is prepared as described in Example 1, dissolved in 10 mL of distilled water. After dying, the hair is washed at least 5 times with distilled water. The original natural white hair will become light black.

Example 3

Mascara Composition in Emulsion Form Containing Peptide-Based Carbon Nanotube Hair Colorant The purpose of this prophetic Example is to describe the preparation of a mascara composition in emulsion form containing the peptide-based carbon nanotube hair colorant, described in Example 1.

The mascara composition is prepared using the following ingredients:

| Chemical or Trade Name | Amount, g |
| --- | --- |
| Triethanolamine stearate | 10 |
| Beeswax | 17 |
| Candelilla wax | 15 |
| Xanthane gum | 1 |
| Propyl para-hydroxybenzoate | 0.15 |
| Peptide-based carbon nanotube hair colorant, prepared as described in Example 1 | 5 |
| Water | qs to 100 |

The waxes are melted. The aqueous phase containing the gums and the peptide-based carbon nanotube colorant is heated to the same temperature as the waxes. The two phases are mixed and stirred vigorously.

Example 4

Mascara Composition in Cake Form Containing Peptide-Based Carbon Nanotube Hair Colorant The purpose of this prophetic Example is to describe the preparation of a mascara composition in cake form containing the peptide-based carbon nanotube hair colorant, described in Example 1.

The mascara composition is prepared using the following ingredients:

| Chemical or Trade Name | Amount, g |
| --- | --- |
| Stearic acid, triple-pressed | 33 |
| Triethanolamine | 12 |
| Glycerol monostearate, self emulsifying | 6 |
| Beeswax | 17 |
| Carnauba wax | 10 |
| Lanolin | 2.8 |
| Castor oil | 6 |
| Propyl para-hydroxybenzoate | 0.2 |
| Peptide-based carbon nanotube hair colorant, prepared as described in Example 1 | 13 |

The waxes, propyl para-hydroxybenzoate, lanolin and castor oil are melted together in a heated mixing kettle, the carnauba wax being added first. The peptide-based carbon nanotube hair colorant is then stirred in and the resulting mass is put through a heated roller mill to ensure adequate dispersion. The mixture is returned to the kettle and the glycerol monostearate, and the triethanolamine are added sequentially. When mixing is complete, the kettle is allowed to cool. Then, the mixture is reheated with slow mixing to avoid the incorporation of air bubbles, and then poured into prepared molds.

Example 5

Eyebrow Pencil Composition Containing Peptide-Based Carbon Nanotube Hair Colorant The purpose of this prophetic Example is to describe the preparation of an eyebrow pencil composition containing the peptide-based carbon nanotube hair colorant, described in Example 1.

The eyebrow pencil composition is prepared using the following ingredients:

| Chemical or Trade Name | Amount, g |
| --- | --- |
| Carnauba wax | 8 |
| Ozokerite | 14 |
| Beeswax | 10 |
| Microcrystalline wax | 14 |
| Hydrogenated oil | 7 |
| Mineral oil | 18 |
| Petrolatum | 18 |
| Lanolin, anhydrous | 2 |
| Propyl para-hydroxybenzoate | 0.3 |
| Peptide-based carbon nanotube hair colorant, prepared as described in Example 1 | 8.5 |
| Ultramarine | 0.2 |

The peptide-based carbon nanotube hair colorant is incorporated into the base wax and dispersed by triple-roll milling, as described in Example 4. The remaining ingredients are added sequentially. When mixing is complete, the mixture is allowed to cool and then is carefully reheated and stirred, and poured into suitable molds.

Example 6

Hair Colorant Composition Containing Peptide-Based Carbon Nanotube Hair Colorant The purpose of this prophetic Example is to describe the preparation of a hair colorant composition containing the peptide-based carbon nanotube hair colorant, described in Example 1.

The hair colorant composition is prepared using the following ingredients:

| Chemical or Trade Name | wt % |
| --- | --- |
| Ammonium lauryl sulfate (anionic surfactant) | 2.00 |
| Propylene glycol (moisturizer) | 4.00 |
| Ethoxydiglycol (solvent) | 2.00 |
| Seaweed extract (conditioner) | 0.80 |
| Tetrasodium EDTA (chelating agent) | 0.80 |
| Isoascorbic acid (antioxidant) | 0.20 |
| Oleic acid (soap) | 12.50 |
| Cetearyl alcohol (opacifier) | 4.00 |
| Emulsifying wax (emulsifier) | 2.00 |
| Oleth-20 (nonionic surfactant) | 1.00 |
| Steareth-21 (nonionic surfactant) | 0.70 |
| Meadowfoam seed oil (oil) | 0.75 |
| Oleyl alcohol (oil) | 0.40 |
| Polyquaternium-10 (cationic surfactant) | 0.20 |
| Polyquaternium-28 (cationic surfactant) | 0.50 |
| Peptide-based carbon nanotube hair colorant, prepared as described in Example 1 | 0.30 |
| Cibafast ® W liquid[2] (UV absorber) | 1.00 |
| Fragrance | 0.75 |
| Wheat amino acids solution | 1.00 |
| Water | qs to 100 |

---

What is claimed is:

1. A diblock, peptide-based carbon nanotube hair colorant having the general structure (HBP)$_n$-CNT, wherein
   a) HBP is a hair-binding peptide;
   b) CNT is a carbon nanotube; and
   c) n ranges from 1 to about 500.

2. A triblock, peptide-based carbon nanotube hair colorant having the general structure [(HBP)$_m$-S]$_n$-CNT, wherein
   a) HBP is a hair-binding peptide;
   b) CNT is a carbon nanotube;
   c) S is a spacer;
   d) m ranges from 1 to about 50; and
   d) n ranges from 1 to about 500.

3. A peptide-based carbon nanotube hair colorant according to claims 1 or 2 wherein the carbon nanotube is either single-walled or multi-walled.

4. A peptide-based carbon nanotube hair colorant according to claims 1 or 2 wherein the carbon nanotube is chemically functionalized.

5. A peptide-based carbon nanotube hair colorant according to claim 4 wherein the chemically functionalized carbon nanotube is produced by a process selected from the group consisting of: oxidation, radical initiation reactions, and Diels-Alder reactions.

6. A peptide-based carbon nanotube hair colorant according to claim 5 wherein the chemically functionalized carbon nanotube is produced by a process comprising the steps of:
   a) providing a population of undispersed carbon nanotubes in solution;
   b) contacting the carbon nanotubes of (a) with a radical generating agent in the presence of acid for a time sufficient to permit the carbon nanotubes to disperse; and
   c) optionally recovering the carbon nanotubes.

7. A peptide-based carbon nanotube hair colorant according to claim 6 wherein the radical generation agent is selected from the group consisting of $(NH_4)_2S_2O_8$, $K_2S_2O_8$, and $Na_2S_2O_8$.

8. A peptide-based carbon nanotube hair colorant according to claim 6 wherein the acid is selected from the group consisting of sulfuric acid, nitric acid, hydrochloric acid and trifluoroacetic acid.

9. A peptide-based carbon nanotube hair colorant according to claim 4 wherein the chemically functionalized carbon nanotube comprises functional groups selected from the group consisting of —COOH, —$PO_4^-$, —$SO_3^-$, —$SO_3H$, —SH, $NH_2$, tertiary amines, quaternized amines, —CHO, and —OH.

10. A peptide-based carbon nanotube hair colorant according to claims 1 or 2 wherein the hair binding peptide is from about 7 to about 45 amino acids.

11. A peptide-based carbon nanotube hair colorant according to claims 1 or 2 wherein the hair binding peptide is selected by a process comprising the steps of:
   a) providing a library of combinatorial generated peptides;
   b) contacting the library of (a) with a hair sample to form a reaction solution comprising peptide-hair complexes:
   c) isolating the peptide-hair complex of (b) from the reaction solution;
   d) amplifying the DNA encoding the peptide portion of the peptide-hair complex of (c); and
   e) sequencing the amplified DNA of (d) encoding a hair-binding peptide wherein the hair-binding peptide is selected.

12. A peptide-based carbon nanotube hair colorant according to claim 11 wherein the DNA encoding the peptides are amplified by a process selected from the group consisting of:
   a) amplifying DNA comprising a peptide coding region; and
   b) infecting a host cell with a phage comprising DNA encoding the peptide.

13. A peptide-based carbon nanotube hair colorant according to claim 11 wherein the library of combinatorial generated peptides is generated by a method selected from the group consisting of phage display, bacterial display, yeast display, and combinatorial solid phase peptide synthesis.

14. A peptide-based carbon nanotube hair colorant according to claim 2 wherein the spacer is selected from the group consisting of ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, palmitoyl alkyl chains, peptides and mixtures thereof.

15. A hair colorant composition comprising an effective amount of the peptide-based carbon nanotube hair colorant of claims 1 or 2.

16. A cosmetic composition comprising an effective amount of the peptide-based carbon nanotube hair colorant of claims 1 or 2.

17. A hair colorant composition according to claim 15 optionally comprising a colorant medium component selected from the group consisting of sequestrants, stabilizers, thickeners, buffers, carriers, surfactants, solvents, antioxidants, polymers, conditioners, and mixtures thereof.

18. A cosmetic composition according to claim 16 optionally comprising a cosmetic medium component selected from the group consisting of oils, waxes, gums, pasty fatty substances, and mixtures thereof.

19. A method of dying hair comprising:
   a) providing a hair colorant composition comprising a peptide-based carbon nanotube hair colorant having the general structure $(HBP)_n$-CNT, or $[(HBP)_m$-S$]_n$- CNT, wherein
      1) HBP is a hair-binding peptide;
      2) CNT is a carbon nanotube;
      3) S is a spacer;
      4) m ranges from 1 to about 50; and
      5) n ranges from 1 to about 500; and b) contacting the hair colorant composition of (a) with hair for a time sufficient for the peptide-based carbon nanotube colorant to bind to hair.

20. A method of coloring eyebrows or eyelashes comprising:
   a) providing a cosmetic composition comprising the peptide-based carbon nanotube hair colorant of having the general structure $(HBP)_n$-CNT, or $[(HBP)_m$-S]-CNT wherein
      1) HBP is a hair-binding peptide;
      2) CNT is a carbon nanotube;
      3) S is a spacer;
      4) m ranges from 1 to about 50; and
      5) n ranges from 1 to about 500; and
      b) contacting the cosmetic composition of (a) with eyebrows or eyelashes for a time sufficient for the peptide-based carbon nanotube hair colorant to bind to eyebrows or eyelashes.

21. A method according to claim 19 wherein step (b) is optionally repeated one or more times.

22. A method according to claim 20 wherein step (b) is optionally repeated one or more times.

23. A method for coloring hair, eyebrows or eyelashes comprising the steps of:
   a) providing a colorant composition selected from the group consisting of:
      i) $(HBP)_n$-CNT; and
      ii) $[(HBP)_m$-S$]_k$-CNT
   wherein
      1) HBP is a hair-binding peptide;
      2) CNT is a carbon nanotube;
      3) n ranges from 1 to about 500
      4) S is a spacer;
      5) m ranges from 1 to about 50; and
      6) k ranges from 1 to about 500;
   and wherein the hair binding peptide is selected by a method comprising the steps of:
      A) providing a library of combinatorial generated peptides;
      B) contacting the library of (A) with a hair sample to form a reaction solution comprising peptide-hair complexes:

C) isolating the peptide-hair complex of (B) from the reaction solution;
D) amplifying the DNA encoding the peptide portion of the peptide-hair complex of (C); and
E) sequencing the amplified DNA of (D) encoding a hair-binding peptide wherein the hair-binding peptide is selected; and b) contacting the colorant composition of (a) with hair, eyebrows or eyelashes for a time sufficient for the peptide-based carbon nanotube colorant to bind to hair, eyebrows or eyelashes.

* * * * *